United States Patent
Whitefield et al.

(10) Patent No.: US 7,312,880 B2
(45) Date of Patent: Dec. 25, 2007

(54) WAFER EDGE STRUCTURE MEASUREMENT METHOD

(75) Inventors: Bruce Whitefield, Camas, WA (US); Jason McNichols, Portland, OR (US); David Sturtevant, Gresham, OR (US)

(73) Assignee: LSI Corporation, Milpitas, CA (US)

( * ) Notice: Subject to any disclaimer, the term of this patent is extended or adjusted under 35 U.S.C. 154(b) by 221 days.

(21) Appl. No.: 10/925,497

(22) Filed: Aug. 24, 2004

(65) Prior Publication Data

US 2006/0044571 A1 Mar. 2, 2006

(51) Int. Cl.
*G01B 11/14* (2006.01)
(52) U.S. Cl. .................................. 356/625
(58) Field of Classification Search ............ 356/625, 356/634
See application file for complete search history.

(56) References Cited

U.S. PATENT DOCUMENTS 6,889,113 B2 * 5/2005 Tasker et al. ............... 700/180
6,895,109 B1 * 5/2005 Schemmel et al. ......... 382/149

* cited by examiner

*Primary Examiner*—Roy M. Punnoose
(74) *Attorney, Agent, or Firm*—Trexler, Bushnell, Giangiorgi & Blackstone, Ltd.

(57) ABSTRACT

A method of determining the distance from an edge feature to a wafer edge. The wafer is put onto an image acquisition tool, and images are captured and classified. Based on the coordinates of the images and their classifications, the distance between an edge feature and the wafer edge is determined. Reference marks can be etched into the wafer to facilitate the measurement. The measurement technique is objective, and can be used to minimize the edge exclusion ring as well as defects that originate from the edge of the wafer.

12 Claims, 4 Drawing Sheets

Provide a Wafer with at Least One Edge Feature that Needs to be Located Relative to the Wafer Edge

↓

Put the Wafer onto an Image Acquisition Tool, Capture and Classify at Least One Image

↓

Calculate the Location of an Edge Feature Based on the Images Which are Captured and Classified

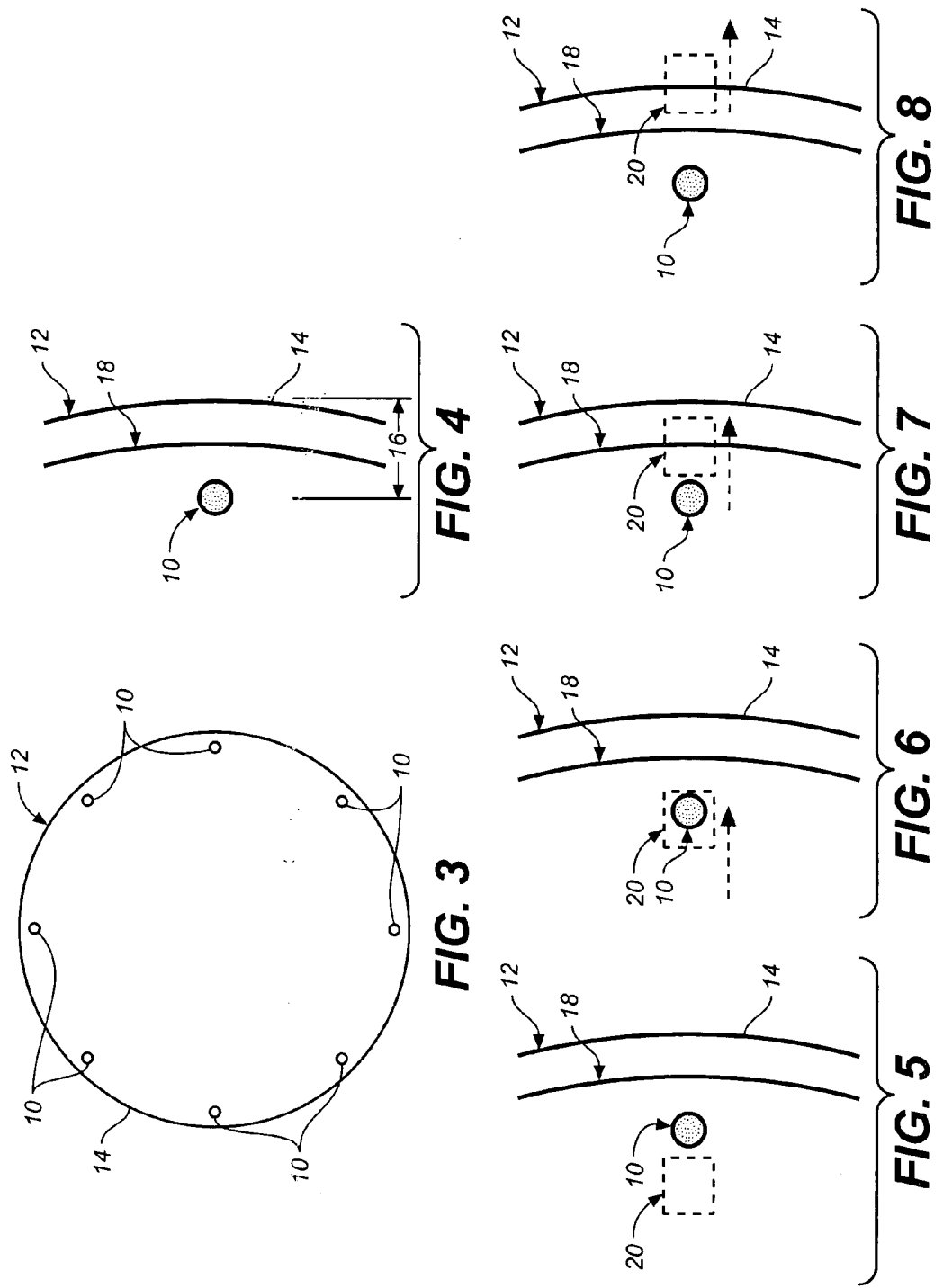

FIG. 9

| Image # | Center of Image | | Distance from Edge | Image Classification |
|---|---|---|---|---|
| | X | Y | | |
| 13 | 0.00 | 196.60 | 3.40 | Other |
| 14 | 0.00 | 196.65 | 3.35 | Other |
| 15 | 0.00 | 196.70 | 3.30 | Other |
| 16 | 0.00 | 196.75 | 3.25 | Other |
| 17 | 0.00 | 196.80 | 3.20 | Align Mark |
| 18 | 0.00 | 196.85 | 3.15 | Align Mark |
| 19 | 0.00 | 196.90 | 3.10 | Align Mark |
| 20 | 0.00 | 196.95 | 3.05 | Align Mark |
| 21 | 0.00 | 197.00 | 3.00 | Align Mark |
| 22 | 0.00 | 197.05 | 2.95 | Align Mark |
| 23 | 0.00 | 197.10 | 2.90 | Align Mark |
| 24 | 0.00 | 197.15 | 2.85 | Align Mark |
| 25 | 0.00 | 197.20 | 2.80 | Align Mark |
| 26 | 0.00 | 197.25 | 2.75 | Other |
| 27 | 0.00 | 197.30 | 2.70 | Other |
| 28 | 0.00 | 197.35 | 2.65 | Other |
| 29 | 0.00 | 197.40 | 2.60 | Other |

| Image # | Center of Image | | Distance from Edge | Image Classification |
|---|---|---|---|---|
| | X | Y | | |
| 41 | 0.00 | 198.00 | 2.00 | Other |
| 42 | 0.00 | 198.05 | 1.95 | Other |
| 43 | 0.00 | 198.10 | 1.90 | Other |
| 44 | 0.00 | 198.15 | 1.85 | Other |
| 45 | 0.00 | 198.20 | 1.80 | Line |
| 46 | 0.00 | 198.25 | 1.75 | Line |
| 47 | 0.00 | 198.30 | 1.70 | Line |
| 48 | 0.00 | 198.35 | 1.65 | Line |
| 49 | 0.00 | 198.40 | 1.60 | Line |
| 50 | 0.00 | 198.45 | 1.55 | Line |
| 51 | 0.00 | 198.50 | 1.50 | Line |
| 52 | 0.00 | 198.55 | 1.45 | Line |
| 53 | 0.00 | 198.60 | 1.40 | Line |
| 54 | 0.00 | 198.65 | 1.35 | Other |
| 55 | 0.00 | 198.70 | 1.30 | Other |
| 56 | 0.00 | 198.75 | 1.25 | Other |
| 57 | 0.00 | 198.80 | 1.20 | Other |

WAFER EDGE STRUCTURE MEASUREMENT METHOD

BACKGROUND

The present invention generally relates to methods for locating edge features of a semiconductor wafer relative to the wafer edge, and more specifically relates to a method for locating the edge features using image classification.

Defects that originate from the edge of a semiconductor wafer have a significant impact on device yields and the number of good die that can be obtained from each wafer. Defects from the wafer edge are caused by the way various films are layered on the edge of the wafer. The manner in which various films stack up on the edge of the wafer differ from that of active device areas. Certain combinations of films layered at the edge of a wafer are undesirable because they tend to flake off during subsequent process steps.

To control how the films stack up at the edge of a wafer, a number of wafer edge processing techniques can be used to limit what films are deposited on the edge, selectively expose edge films to normal etch processes, or selectively etch the edge films. Specifically, commonly used techniques include:

1. Wafer edge resist exposure (WEE).
2. Resist and Barc removal using edge solvent dispense.
3. Thin film deposition edge exclusion rings (shadow or gas exclusion).
4. Wafer edge etch to remove unwanted films.

The exact settings used for edge film definition can dramatically affect the yields of a wafer by modulating the number of particle defects coming from the wafer edge. In photo lithography, edge removal process settings are used to control edge film patterning and prevent inappropriate edge film combinations.

In addition to controlling the edge film stacks to reduce defects, it is also important that this be performed in the smallest ring possible around the edge of the wafer. The so-called "edge exclusion ring" is the portion of the wafer edge that is sacrificed for the edge film control. Typically, a 3 or 4 millimeter ring around the edge of the wafer is considered to be unusable. This is a significant area of the wafer that will not produce yielding die.

With very accurate control of the edge settings, it is possible to shrink this edge exclusion zone to 2 millimeters or even smaller while still maintaining film stack combinations that minimize edge defects. Narrower edge settings can achieve an improvement in whole die per wafer. For example, the difference between a 3 millimeter edge setting and a 2 millimeter edge setting can be worth an additional 10 to 30 die per wafer, depending on die size. Even with the lower yields of edge die, the increase in gross die per wafer represents a significant financial value for a typical wafer fabrication laboratory. Presently, at a run rate of 2000 wafers per week, an extra 12 die per wafer would be worth an extra $58,000 per week (or $696,000 per year), with no additional processing cost.

In order to control wafer edge effects, it is critical to precisely control the edge exclusion and edge removal settings. Experience has proven that +/−0.2 millimeter control is needed to achieve consistent results with a 2 millimeter edge setting.

The problem this level of control poses involves how to accurately and inexpensively measure the edge settings of various wafer fabrication processes in order to maintain control of the wafer edge.

A current method for edge setting control is for an operator or technician to view the wafer edge under a microscope. Specifically, the operator estimates the distance from the edge setting to the edge of the wafer based on the magnification used and approximate distance in the field of view. This is repeated at several positions around the edge of the wafer to check for centering of the pattern. The problem with this approach is that the measurement is very subjective and inaccurate (i.e., different people can obtain different measurements of the same thing). The technique can be improved by using an optical vernier or grid on the microscope objectives, but it still cannot provide the accuracy and repeatability needed to meet a +/−0.2 millimeter requirement.

A second approach is to use critical dimension (CD) measurement tools such as a critical dimension (CD) semi-electron microscope (SEM) to measure the distance from the edge of the wafer to an edge feature. The problem with this approach is that these tools can be very expensive (presently about $1,000,000), and are generally designed to measure features that are orders of magnitude smaller. As such, it is very difficult to get the wafer edge and edge feature within the same field of view. Additionally, these tools are usually in great demand to support the critical CD measurement needs for which they were originally purchased.

A third approach is to purchase a dedicated optical measurement tool that is specifically designed for the appropriate scale of measurements. This method can provide adequate resolution, but can be expensive (presently about $500,000). Additionally, generally it is cost prohibitive to buy a tool for this single application. Even with such an instrument, the fact that different people may obtain different sets of measurements while measuring the same thing (i.e., variability from person to person in taking the measurements) remains an issue.

OBJECTS AND SUMMARY

An object of an embodiment of the present invention is to locate edge features so that defects that originate from the edge of a semiconductor wafer can be minimized.

Another object of an embodiment of the present invention is to locate edge features so that the edge exclusion ring of the wafer can be minimized.

Still another object of an embodiment of the present invention is to control edge settings using an objective measurement technique.

Briefly, and in accordance with at least one of the foregoing objects, an embodiment of the present invention provides a method of determining the distance from an edge feature to a wafer edge. The wafer is put onto an image acquisition tool, and images are captured and classified. Based on the coordinates of the images and their classifications, the distance between an edge feature and the wafer edge is determined.

Reference marks can be used to facilitate the measurement. Specifically, a test wafer can be built, wherein a recognizable pattern such as a plurality of reference marks is etched into the wafer at a known distance from the wafer edge. Then, the wafer is processed, thereby providing that the wafer has edge features which need to be measured relative to the wafer edge. Then, the wafer is placed onto an image acquisition tool, and images are captured of at least one of the reference marks and an edge feature (as well as possibly also the wafer edge). The images are classified, and coordinates are noted. From the images, their classifications and coordinates, the distance between an edge feature and the wafer edge is determined, based on the location of the reference mark.

BRIEF DESCRIPTION OF THE DRAWINGS

The organization and manner of the structure and operation of the invention, together with further objects and advantages thereof, may best be understood by reference to the following description, taken in connection with the accompanying drawings, wherein:

FIGS. 3-8 are views which relate to the method shown in FIG. 2; and

FIG. 9 provides two portions of a list of images, their coordinates, distance from the wafer edge, and classification.

DESCRIPTION

Figure 1:
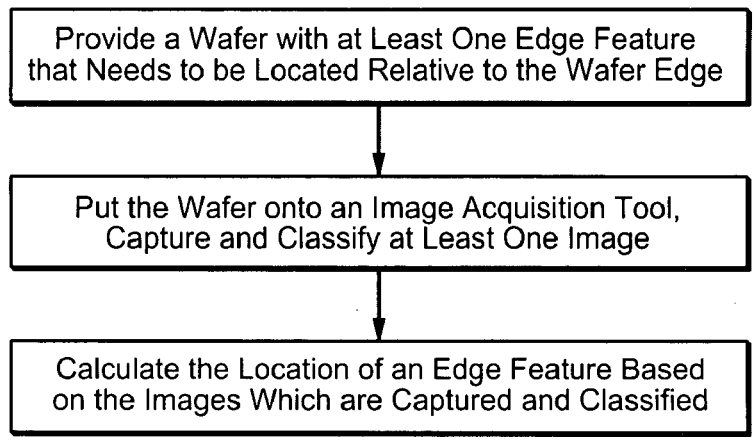
FIG. 1 provides a flow chart which illustrates a method which is in accordance with an embodiment of the present invention.

While the invention may be susceptible to embodiment in different forms, there are shown in the drawings, and herein will be described in detail, specific embodiments of the invention. The present disclosure is to be considered an example of the principles of the invention, and is not intended to limit the invention to that which is illustrated and described herein.

The present invention provides for the use of image classification to determine the distance from an edge feature to a wafer edge. The measurement technique is objective, and can be used to minimize the edge exclusion ring as well as defects that originate from the edge of the wafer.

As shown in FIG. 1, the method provides that a wafer is processed to provide at least one edge feature on the wafer which needs to be located relative to the wafer edge. Then, the wafer is placed onto an image acquisition tool, such as onto an automated optical review microscope, or a defect inspection and automated review SEM which has image acquisition capability. The image acquisition tool is programmed to go to programmed locations on the wafer, capture an image and record the wafer co-ordinate location of that image. The image acquisition tool is used to capture images, and the images are classified using image classification techniques (Automatic Defect Classification, or ADC). Then, the location of the edge feature relative to the wafer edge is calculated based on the images which have been captured and classified. Specifically, the image that is classified as having a "defect" of a line running through the pattern is assumed to be the image of an edge feature. The coordinate(s) associated with this image is then used to determine the location of the edge feature.

Figure 2:
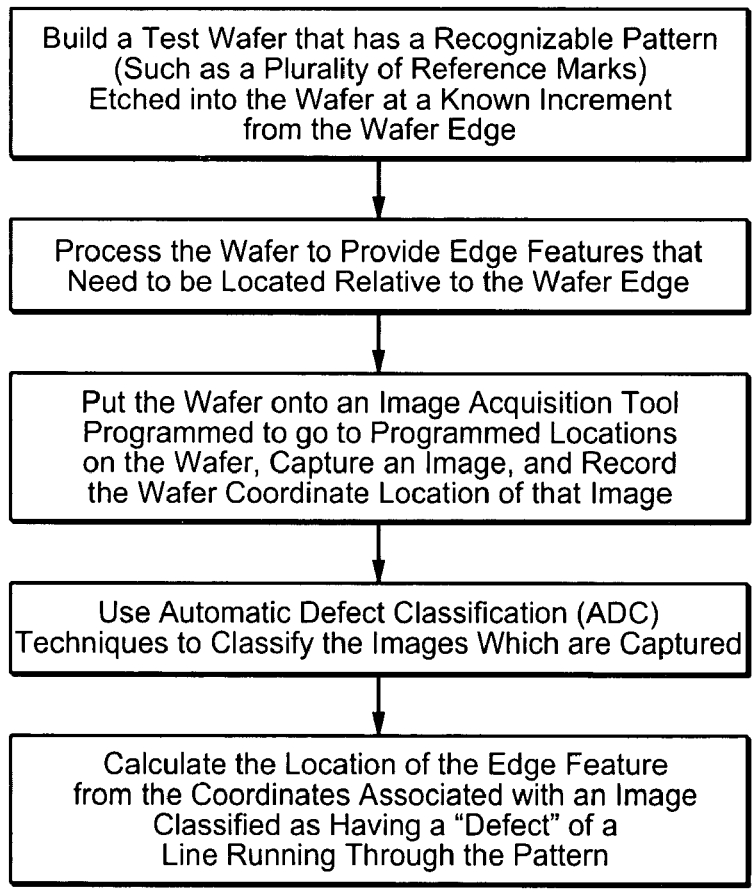
FIG. 2 provides a flow chart which illustrates a method which is in accordance with another embodiment of the present invention.

A recognizable pattern can be etched into the wafer to facilitate the calculation, in which case the method would be as shown in FIG. 2. In such a method, a test wafer is first built to provide a recognizable pattern on the wafer. For example, as shown in FIG. 3, eight reference marks 10 can be etched into the wafer 12, where each of the marks is positioned a predetermined distance from the wafer edge 14.

The reference marks can be any shape that is easily recognizable to the image classification or pattern recognition system and can be placed in any convenient location. For example, as shown in FIG. 4, on a 200 millimeter wafer, each reference mark can be provided 3 millimeters (dimension 16) from the wafer edge 14. The test wafer is then processed through the tool of interest to create the edge removal pattern (in FIG. 4, reference numeral 18 identifies an edge feature) that needs to be measured.

As shown in FIG. 2, after processing, the wafer 12 is placed on an image capture system such as an optical inspection microscope with an automatic wafer stage and camera system to capture optical images. The microscope is programmed to drive to a location at or near the reference mark and start taking a series of images as it steps the image field over the reference mark and edge removal line. The microscope may be programmed to step 0.05 millimeters at a time.

FIGS. 5 through 8 illustrate a series of images, wherein box 20 is the image field. FIG. 5 illustrates an image taken to the left of a reference mark 10. FIG. 6 illustrates a subsequent step, wherein an image of the reference mark 10 is captured. FIG. 7 illustrates a subsequent step, wherein an image of the edge feature 18 is captured. If desired, the microscope can be stepped beyond the edge feature 18 to the wafer edge 14 as shown in FIG. 8.

Each image is classified using automatic defect classification (ADC) or pattern recognition techniques that are commonly available. The image classification is quite simple since it only needs to accurately classify the reference mark and the edge line apart from any other patterns that appear in an image.

The result is a table of data that correlates the image classification to the position (such as x and y coordinates) of the image. FIG. 9 illustrates two portions of the table that are of interest, which include the images that have captured a reference mark (in FIG. 9, image classification "Align Mark") and images which have captured an edge feature (in FIG. 9, image classification "Line").

From this information, it is quite simple to calculate the location of the reference mark and edge feature by finding the center of the block of images that have captured the desired image. In the case shown in FIG. 9, the reference mark is located at:

Mark $Y=(Min_Y-Min_Y)/2+Min_Y->(3.2-2.8)2+2.8=3.0$ mm from edge.

Similarly, the location of the edge feature is located at:

Line$_Y=(Min_Y-Min_Y)/2+Min_Y->(1.8-1.4)2+1.4=1.6$ mm from edge.

Once calculated, this data can used to provide feedback to the user or entered into a factory SPC system for trending and analysis.

The present invention provides for:
1. Use of automated image acquisition and/or pattern recognition systems to capture images of wafer edge structures at known locations on the wafer edge.
2. Use of Automatic Defect Classification (ADC) and/or pattern recognition techniques to provide a classification of the edge structures captured by the image acquisition tool.
3. Use of the above data to calculate the location of the edge structures relative to the wafer edge or center.
4. Use of a machine or ADC recognizable alignment mark to improve accuracy of edge structure measurements.

The key advantages of this method are:
1. Enable accurate edge structure measurements by utilizing tools that are already available in wafer Fabs.
2. Improved accuracy over current or alternative methods used to make edge measurements.
3. Provides an automated measurement method that requires less user time to perform and reduces error induced by subjective measurement techniques.
4. Automating the edge structure measurement method and feeding the results directly to a factory database of SPC control system for trend charting, analysis and alarm notifications.

An alternative that can be applicable to some processes is to use a blank wafer and rely entirely on the image capture tool stage resolution to determine what image has the edge film line in it. This avoids the need for any reference marks with some trade off in accuracy of the measurement.

Figure 10:
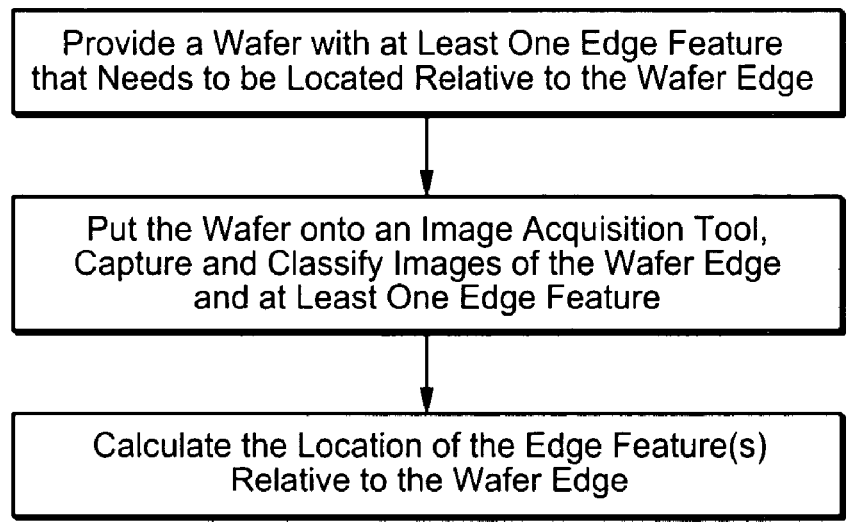
FIG. 10 provides a flow chart which illustrates a method which is in accordance with yet another embodiment of the present invention.

A further variant for avoiding the need for the reference marks is to use the edge of the wafer itself as an alignment mark, in which case the method would be as shown in FIG. 10. This would require that the ADC or pattern recognition system be able to accurately identify the wafer edge which can be a problem for some systems since it may be out of the focus range of the tool.

Another version would be to use product wafers instead of test wafers to perform this measurement. In this case there may be existing patterns that could be used for alignment purposes. This method may be applicable only to layers that are relatively early in the manufacturing process since the multiple lines and edge structures which occur on product wafer late in the process flow can be confounding for the ADC or pattern recognition systems.

A further variant on using product wafers would be to place edge alignment marks on product wafers at the very edge of the wafer, beyond the usable area of the wafer. This could provide accurate measurement capability on product wafers without sacrificing yieldable wafer surface, although it would add somewhat to the cost of making the wafers.

While embodiments of the present invention are shown and described, it is envisioned that those skilled in the art may devise various modifications of the present invention without departing from the spirit and scope of the appended claims.

What is claimed is:

1. A method of determining a distance from an edge feature to a wafer edge, said method comprising: using an image acquisition tool to start at a pre-determined location on the wafer and step linearly across the wafer and capture a plurality of equally spaced-apart images of the wafer; having the image acquisition tool classify the images and note at least one coordinate associated with each image; using the classifications of the images and their coordinates to determine the distance between the edge feature and the wafer edge; and at least one of using data to provide feedback to a user or outputting results to a database of a control system for analysis.

2. A method as recited in claim 1, wherein the step of using the image acquisition tool to capture images of the wafer comprises using an optical review microscope to capture the images.

3. A method as recited in claim 1, wherein the step of using the image acquisition tool to capture images of the wafer comprises using an automated review SEM which has image acquisition capability to capture the images.

4. A method as recited in claim 1, further comprising forming a pre-determined pattern on the wafer.

5. A method as recited in claim 4, wherein the step of forming a pre-determined pattern on the wafer comprising forming a plurality of reference marks on the wafer, a pre-determined distance from the wafer edge.

6. A method as recited in claim 5, further comprising using the image acquisition tool to capture a plurality of images including images of the edge feature and at least one of the reference marks.

7. A method as recited in claim 6, further comprising using the image acquisition tool to capture at least one image of the wafer edge.

8. A method as recited in claim 5, wherein the step of using the image acquisition tool to capture images of the wafer comprises moving a microscope across the wafer, and using the microscope to capture a plurality of images including images of the edge feature and at least one of the reference marks.

9. A method as recited in claim 8, further comprising using the microscope to capture at least one image of the wafer edge.

10. A method as recited in claim 1, wherein the step of using the image acquisition tool to classify the images comprises using an automatic defect classification technique to classify the images.

11. A method as recited in claim 10, further comprising concluding that an image that has been classified as having a defect of a line running through a pattern comprises an image of the edge feature.

12. A method as recited in claim 1, wherein the step of using the image acquisition tool to capture images of the wafer comprises moving a microscope across the wafer.

* * * * *